United States Patent
Leussler et al.

(10) Patent No.: US 11,850,033 B2
(45) Date of Patent: Dec. 26, 2023

(54) RF COIL WITH INTEGRATED VITAL SIGNS DETECTOR

(71) Applicant: KONINKLIJKE PHILIPS N.V., Eindhoven (NL)

(72) Inventors: Christoph Günther Leussler, Hamburg (DE); Daniel Wirtz, Hamburg (DE); Julien Thomas Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/788,318

(22) PCT Filed: Dec. 22, 2020

(86) PCT No.: PCT/EP2020/087584
§ 371 (c)(1),
(2) Date: Jun. 23, 2022

(87) PCT Pub. No.: WO2021/130203
PCT Pub. Date: Jul. 1, 2021

(65) Prior Publication Data
US 2023/0037196 A1 Feb. 2, 2023

(30) Foreign Application Priority Data
Dec. 23, 2019 (EP) .................................... 19219362

(51) Int. Cl.
*A61B 5/055* (2006.01)
*A61B 5/302* (2021.01)
*A61B 5/08* (2006.01)
*G01R 33/36* (2006.01)
*G01R 33/567* (2006.01)

(52) U.S. Cl.
CPC ............ *A61B 5/055* (2013.01); *A61B 5/0816* (2013.01); *A61B 5/302* (2021.01); *G01R 33/3621* (2013.01); *G01R 33/5673* (2013.01); *A61B 2562/0214* (2013.01)

(58) Field of Classification Search
None
See application file for complete search history.

(56) References Cited

U.S. PATENT DOCUMENTS 8,098,149 B2   1/2012  Fisher et al.
2012/0172738 A1*  7/2012  Gleich ................ A61B 5/0515
                                                600/509

(Continued)

FOREIGN PATENT DOCUMENTS

WO   2014141109 A1   9/2014

OTHER PUBLICATIONS

P. Richardson, "The insulated electrode: A pasteless electrocardiogramachnique," in 20th Ann. Conf. on Engineering in Medicine and Biology, vol. 15.7, 1967.

(Continued)

*Primary Examiner* — Rodney E Fuller (57) ABSTRACT

A radio frequency (RF) transmit—receive coil for a magnetic resonance (MR) imaging system includes an integrated vital signs detector for the detection of vital signs of a patient within the MR imaging system. The coil includes a contactless sensor system for monitoring vital signs, which makes it easier to measure vital signs of the patient.

13 Claims, 6 Drawing Sheets

(56) References Cited

U.S. PATENT DOCUMENTS

| | | |
|---|---|---|
| 2014/0197836 A1 | 7/2014 | Hamamura et al. |
| 2015/0087959 A1 | 3/2015 | Rossler |
| 2015/0223717 A1* | 8/2015 | Govari ................ A61B 5/333 600/411 |

OTHER PUBLICATIONS

J. Schneider, C. Koellner, and S. Heuer, "An approach to automotive ECG measurement validation using a car-integrated test framework," in Intelligent Vehicles Symposium, 2012 IEEE, 2012, pp. 950-955.

M. Czaplik, B. Eilebrecht, R. Walocha, M. Walter, P. Schauerte, S. Leonhardt, and R. Rossaint, "The reliability and accuracy of a noncontact Electrocardiogramhic System for Screening Purposes" Int. Anesthesia Research Soc. Feb. 2012, vol. 114, No. 2.

S.N. Asl et al, "Noise Properties of Textile, Capacitive EEG Electrodes" Current Directions in Biomedical Engineering 2015; 1:34-37.

Li et al "Monostructure Touch Sensor with Multifunctional for Discrimination of Material Properties" Electrical Engineering in Japan, vol. 117, No. 3, 1996.

P.J. French et al Sensors for Catheter Applications, p. 365-366 Jan. 8, 2004.

Guger et al "Comparison of Dry and Gel Based Electrodes for P300 Brain Computer Interfaces" Frontiers in Neuroscience, May 7, 2012.

International Search Report and Written Opinion from PCT/EP2020/087584 dated Apr. 15, 2021.

\* cited by examiner

RF COIL WITH INTEGRATED VITAL SIGNS DETECTOR

CROSS REFERENCE TO RELATED APPLICATIONS

This application is a U.S. national phase application of International Application No. PCT/EP2020/087584 filed on Dec. 22, 2020, which claims the benefit of EP Application Serial No. 19219362.1 filed on Dec. 23, 2019 and is incorporated herein by reference.

FIELD OF THE INVENTION

The invention relates to the field of radio frequency (RF) transmit-receive coils for a magnetic resonance (MR) imaging system and in particular to a RF transmit-receive coil with an integrated vital signs detector. The invention also relates to a system for the detection of vital signs of a patient within a magnetic resonance (MR) imaging system, to a method for operating the system for the detection of vital signs of a patient within a magnetic resonance (MR) imaging system, a software package for a magnetic resonance (MR) imaging system and a software package for upgrading a magnetic resonance (MR) imaging system.

BACKGROUND OF THE INVENTION

High quality triggering in medical imaging (especially MR) is vital for a large number of examinations, e.g. cardiac-, abdominal- or pelvis-imaging. Only with good quality trigger signals the imaging sequence can be carried out at equal expiration states or equal points during the cardiac cycle resulting in superior image quality. Typically, vital signs are recorded using dedicated sensors, which are expensive as well as prone to errors and misplacements. Today, the ECG is used to determine the heartbeat and therewith trigger the imaging device. However, the ECG requires additional effort in preparing the patient (mount and wire electrodes, connect an activate the wireless transmitter). Capacitive electrodes for the evaluation of human body bioelectric potentials are a very attractive alternative to conventional galvanically coupled electrodes for diagnostic applications especially when the signals have to be measured through insulating materials like cloth, which would greatly simplify the current procedure Capacitive type electrodes are able to detect bio potentials with an explicit gap between the sensor and the body, even through hair and clothing. Compared to standard conductive type electrodes, the surface of these electrodes is electrically insulated and thus remains stable even in long-term applications. The sensor's metal electrode and the body surface are capacitively coupled, forming a capacitance As such, the capacitive type electrodes detects the so-called displacement current ID, posited by J. C. Maxwell to explain magnetic fields around a capacitor, which is proportional to the rate of change of the electric field associated with the ECG signal.

From the document EP2020916 A2 a wireless patient monitor for MRI is known wherein a patient, supported on a movable table, may be positioned outside the bore of the magnet to receive a wireless patient monitor receiving signals from the patient by leads. The patient may then be moved into the bore of the magnet with the wireless patient monitor allowing for continuous monitoring of the patient. The wireless patient monitor may incorporate its own power supply to transmit the monitored signals from the patient via radio transmitted signal or the like to a base station positioned near the magnet but outside of the bore. However, the patient monitor requires additional effort in preparing the patient e.g. mounting and wiring electrodes and connecting the wireless transmitter.

SUMMARY OF THE INVENTION

It is an object of the invention to provide a radio frequency (RF) transmit-receive coil for a magnetic resonance (MR) imaging system with an integrated vital signs detector for the detection of vital signs of a patient within the magnetic resonance (MR) imaging system, whereby contact sensors directly attached to the body of the patient, are replaced by a contactless system for monitoring vital signs, which makes it much easier to measure vital signs of the patient.

According to the invention, this object is addressed by the subject matter of the independent claims. Preferred embodiments of the invention are described in the sub claims.

Therefore, according to the invention, a radio frequency (RF) transmit-receive coil for a magnetic resonance (MR) imaging system is provided, the RF transmit-receive coil comprising a vital signs detector for the detection of vital signs of a patient within the magnetic resonance (MR) imaging system, wherein the vital signs detector is integrated in the RF transmit-receive coil, wherein a pair of electrically conducting coil elements of the RF transmit-receive coil forms the vital signs detector, wherein the vital signs detector is a capacitive vital signs detector, the capacitive vital signs detector being adapted for receiving capacitive vital signs signals. The proposed system consists of a combination of a RF transmit-receive coil with a capacitive vital signs detector for real time vital signs monitoring and simultaneous high-resolution imaging. The capacitive vital signs detector is formed by the conductors of the RF transmit-receive coil. The method is therefore entirely passive as it utilizes the measurement of the local electric field as modified by the movement of the body (particularly the respiration and cardiac activity). Furthermore, combining RF coil and capacitive vital signs sensor techniques provides improved signal quality using cross correlations between systems, improved calibration schemes, or (spatial) guidance of one system using the other. In an embodiment of the invention the magnetic resonance (MR) imaging system can also be a MR-Therapy system like a MR-LINAC.

In an embodiment of the invention the capacitive vital signs detector is an electrocardiography (ECG) sensor being adapted for receiving ECG signals.

According to an embodiment of the invention the pair of electrically conducting coil elements of the RF transmit-receive coil forming the vital signs detector are covered with a material having a high permittivity. To increase the capacitance of the detector to the human body, the electrodes may be covered with a material having a high permittivity, such as ceramic. Electrodes are integrated in the coil cover (close to the body surface), thus no galvanic contact and galvanically isolated to human body. The capacitance ECG depends on several factors, but usually corresponds to relatively small values between 0.1-10 pF. For low frequency measurements as the ECG, such weak coupling requires high input impedance of the sensor as finite input resistance would attenuate the input voltage $V_{in}$. Very high impedance nodes are very susceptible to any electromagnetic interference from the environment and motion induced artefacts. Therefore, in an advantageous embodiment of the invention the electrodes can be actively shielded in order to suppress the interference.

In another preferred embodiment of the invention the capacitive vital signs detector and the RF transmit-receive coil being adapted for processing the capacitive vital signs signal and an MRI signal acquired by the RF transmit-receive coil in different frequency spaces.

In an embodiment of the invention the vital signs detector is arranged beneath a patient support of a magnetic resonance (MR) imaging system. The arrangement of the detector below a patient support is advantageous, as ECG can be received here especially well. This position is also particularly advantageous for measuring movements and the position of the patient.

In another aspect of the invention, the object is achieved by a system for the detection of vital signs of a patient within a magnetic resonance (MR) imaging system, the system comprising: a radio frequency (RF) transmit-receive coil with a vital signs detector according to any of claims 1 to 4, the system further comprising an output pre-amplifier for amplifying the capacitive vital signs signals, wherein the pair of electrically conducting coil elements is coupled to the output pre-amplifier, the system further comprising a digital signal processor, wherein the digital signal processor being adapted for further processing the amplified capacitive vital signs signals.

According to a preferred embodiment the digital signal processor is a software defined radio (SDR). SDR's typically comprise analog-to-digital and digital-to-analog converters, RF components for transmitting and/or receiving of signals an, a FPGA for basic filtering, signal down- and up-conversion and bidirectional wireless or optical outputs. The software exists in the computer, where it is executed and sends instructions to the SDR. A received signal is amplified e.g. by a preamp, and returned to the radio where it can be further amplified or attenuated. The ADC converts the signal to a digital signal, where the FPGA and digital signal processor (DSP) handle down converting and filtering the digital signal. The data stream is then returned to the computer and real time signal processing software.

According to another embodiment of the invention the system comprises a relaxation oscillator and/or a microcontroller for the capacitive vital signs signals detection.

In another preferred embodiment of the invention the system comprises a multiplexer for switching between different pairs of electrically conducting coil elements of the RF transmit-receive coil forming the vital signs detector.

In a further aspect of the invention, the object is achieved by a method for operating the system for the detection of vital signs of a patient within a magnetic resonance (MR) imaging system as described above comprising the following steps:
  providing a radio frequency (RF) transmit-receive coil comprising a vital signs detector, wherein the radio frequency (RF) transmit-receive coil and the vital signs detector form a magnetic resonance (MR) imaging coil array,
  receiving at least one vital signs signal from the vital signs detector,
  receiving at least one MM signal from the radio frequency (RF) transmit-receive coil,
  performing a correction of the MM signal based on the vital signs signal.

According to an embodiment of the invention the step of performing a correction of the MRI signal based on the vital signs signal comprises a correction based on a deep learning algorithm.

In a still further aspect of the present invention, the object is achieved by a magnetic resonance (MR) imaging system comprising a system for the detection of vital signs of a patient as described above.

In a further aspect of the invention, the object is achieved by a software package for a magnetic resonance (MR) imaging system, whereby the software package contains instructions for controlling a system for the detection of vital signs of a patient within a magnetic resonance (MR) imaging system according to the method as described above.

In another aspect of the invention, the object is achieved by a software package for upgrading a magnetic resonance (MR) imaging system, whereby the software package contains instructions for controlling a radio frequency (RF) receiver system comprising a vital signs detector according to the method as described above.

In an embodiment of the invention an AI-based software algorithm for selecting the capacitive electrodes from sensor data and for configuring e.g. filter parameters based on training data obtained with the system can be foreseen. The data can be processed and filtered using e.g. Kalman or SVD filtering. Data processing can, for example, take place remotely in a cloud.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
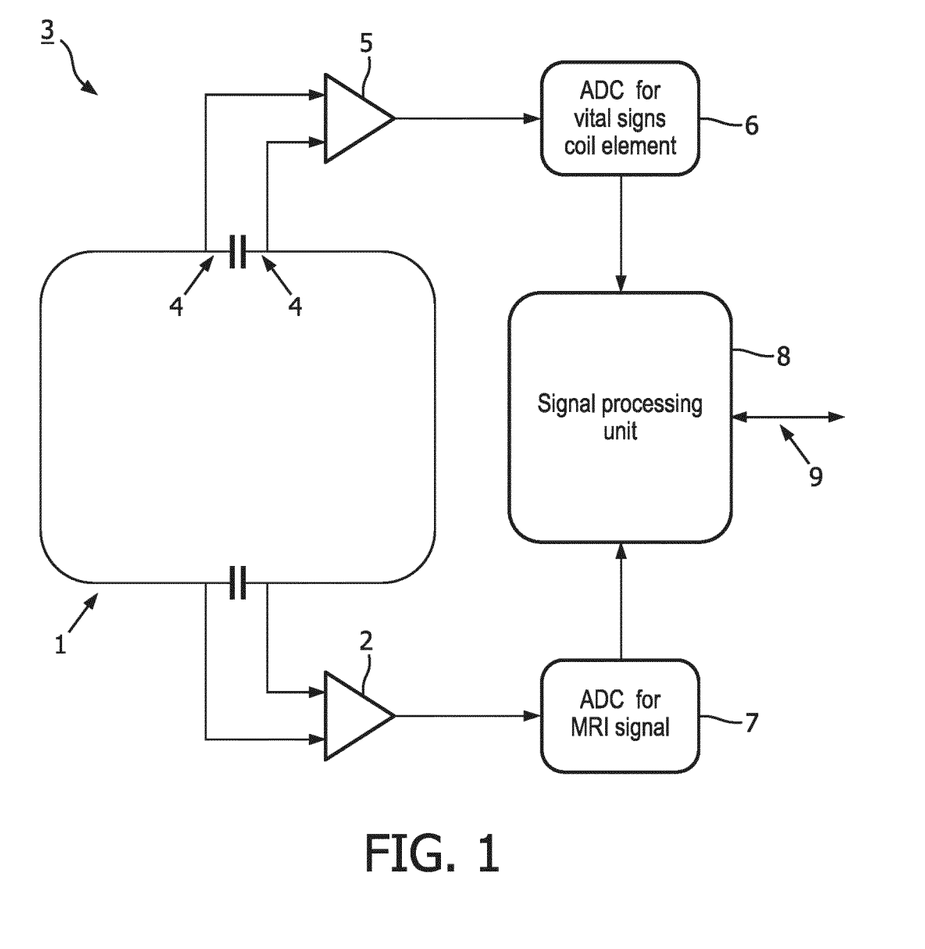
FIG. 1 schematically depicts a system for the detection of vital signs comprising a radio frequency (RF) transmit-receive coil with a vital signs detector according to an embodiment of the invention, FIG. 2 schematically depicts a system for the detection of vital signs comprising a radio frequency (RF) transmit-receive coil with a vital signs detector according to another embodiment of the invention, FIG. 3 schematically depicts a part of a system for the detection of vital signs according to another embodiment of the invention, FIG. 4 schematically depicts a flow chart of the signal stream of the vital signs detector and the RF transmit-receive coil according to an embodiment of the invention.

FIG. 1 schematically depicts a system for the detection of vital signs comprising a radio frequency (RF) transmit-receive coil 1 with a vital signs detector 3 according to an embodiment of the invention. The conductor 4 of the radio frequency (RF) transmit-receive coil 1 forms a capacitive electrode with a coupling to the body which is in the order of 5-20 pF. The induced ECG signal can be measured as change in the capacitance. For example, a voltage signal is measured over the capacitance and amplified via the high impedance preamplifier 5. Additionally the capacitance can be modulated by the motion of the body. Having a RF coil array 18, each individual measured signal depends on the local motion and local ECG signal. The amplified signal is further digitally processed e.g. via a FPGA unit 8. The MRI signal of RF transmit-receive coil 1 is received by the resonant coil circuit and amplified by a RF preamplifier 2. Due to the high impedance of the ECG preamplifier 5 the RF signal is not disturbed. The RF transmit-receive coil signal is further digitized and can be used for correction and calibration of the ECG signal, e.g. to remove motion induced artefacts.

The capacitive vital signs signals and the MRI signals are processed in different frequency spaces. Therefore, in an embodiment of the invention two separate ADC channels 6, 7 may be provided. The output of the ADCs is fed to a signal processing device 8. The signal processing device 8 can be e.g. a software defined radio (SDR). The signal processing device 8 can be used e.g. for the correction of motion artefacts in the MRI signal by the vital signs signals. An interface 9 e.g. an optical interface, controls the communication of the signal processing device 8 with other components of the MM system. As well other circuits schemes can be realized with only one common ADC. In another embodiment of the invention the capacitive sensor signal can be transformed (or modulate a) to a pilot tone and received via the MM receiver or by separate receiver at a different frequency.

The detection of motion e.g. by breathing or heart beat is one application of the vital signs detector 3, additionally the capacitive vital signs signals can be simultaneously processed by other vital signs detectors such as cameras or RADAR sensors.

Figure 2:
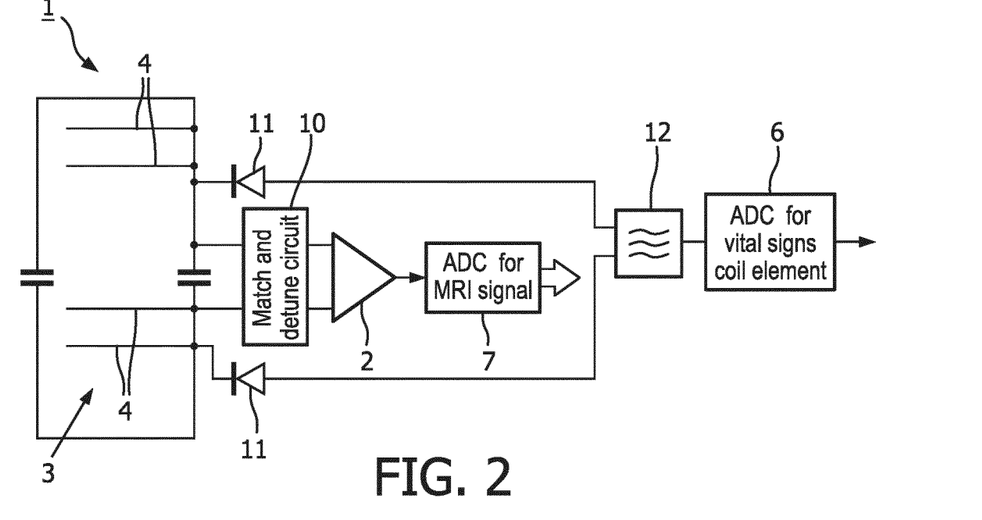

FIG. 2 schematically depicts a system for the detection of vital signs comprising a radio frequency (RF) transmit-receive coil 1 with a vital signs detector 3 according to another embodiment of the invention. In FIG. 2 the RF transmit-receive coil 1 is shown with four capacitive conductors 4 forming the capacitive vital signs detector 3. The conductors 4 increase the capacitance for the ECG signal, while the MRI coil resonance is determined by the loop conductor and the lumped capacitors. The MRI signals are received by electrically conducting coil elements of the RF transmit-receive coil 1 and fed to a match and detune circuit 11, amplified by a RF amplifier 2 and further fed to an analog-to-digital converter (ADC) 7. The capacitive vital signs signals are received by the capacitive conductors and fed via two diodes 11 to a relaxation oscillator 12 or a microcontroller for the detection of the capacitive vital signs signals.

Figure 3:
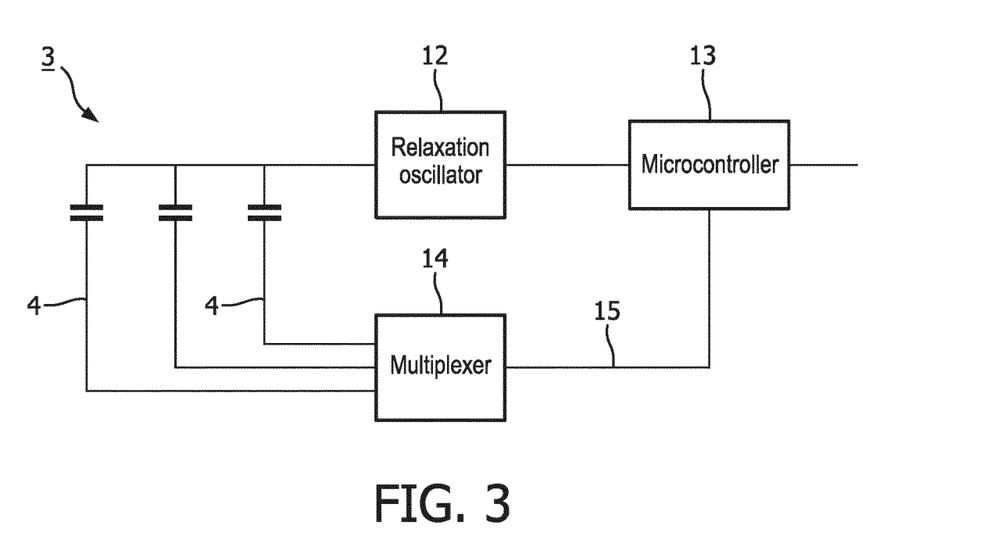

FIG. 3 schematically depicts a part of a system for the detection of vital signs according to another embodiment of the invention. In an embodiment of the invention several electrically conducting coil elements 4 of the RF transmit-receive coil 1 forming vital signs detectors 3 can be foreseen. In order to be able to switch between different vital signs detectors 3, a multiplexer 14 is provided which is controlled, for example, by means of a microcontroller 13 by a control signal 15. Also, in this embodiment a relaxation oscillator 12 can be provided for the detection of the vital signs signals.

Figure 4:
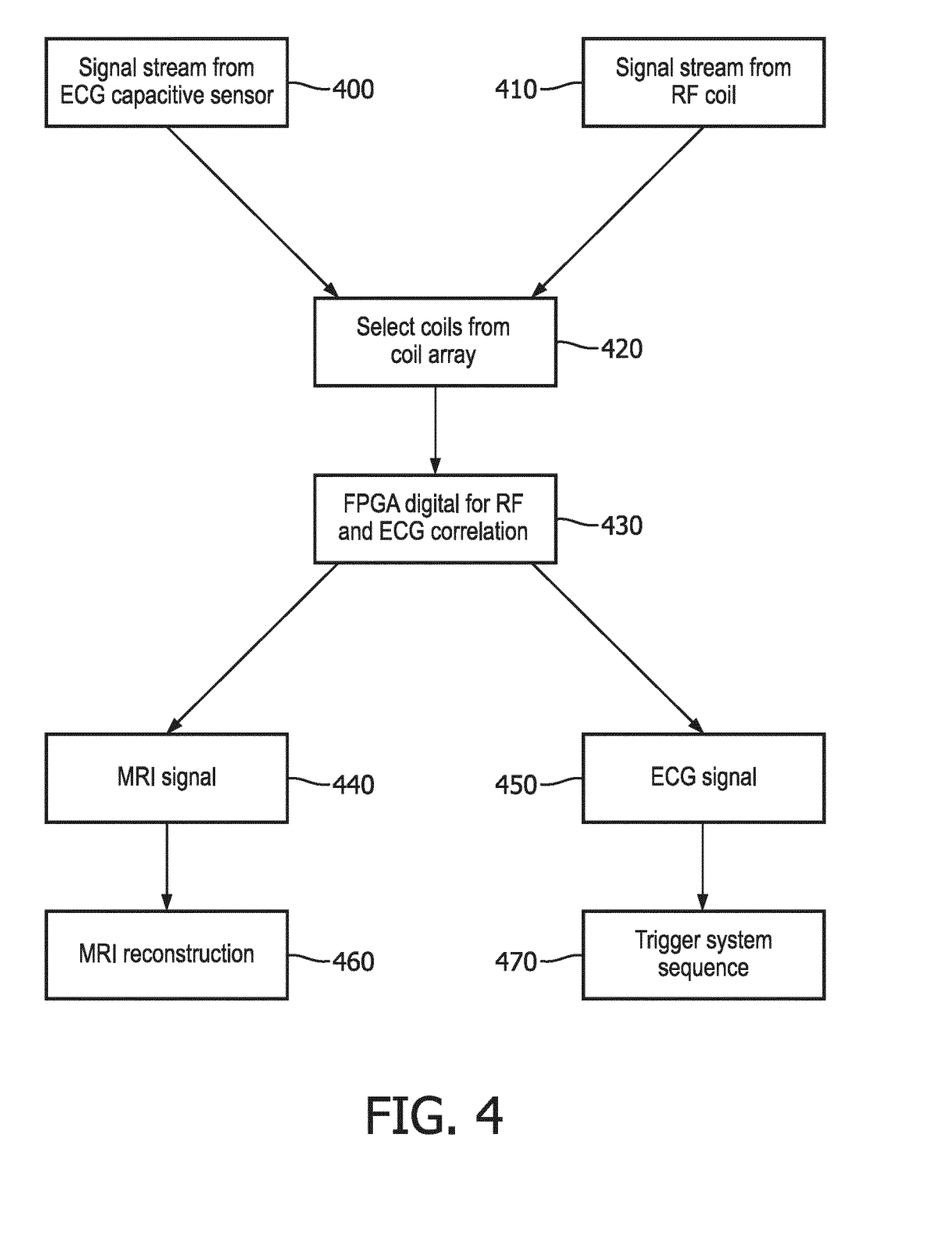

FIG. 4 schematically depicts a flow chart of the signal stream of the vital signs detector 3 and the RF transmit-receive coil 1 according to an embodiment of the invention. The vital signs signal from the vital signs detector 3 is analyzed in step 400. The MM signal from the RF transmit-receive coil 1 is analyzed in step 410. In step 420 the best signal is identified either from the vital signs detector 3 or the RF transmit-receive coil 1. Afterwards a signal processing device 8 e.g. a software defined radio (SDR) is used for generating a correlation of the signal in step 430. An improved trigger signal can then be generated from the vital sign signal 450 for improved control of the MRI signal in step 470, e.g. using the correlation of both signals. The MRI signal 440 can also be improved using the vital signs signal. For example, the overall signal quality can be improved by setting a range of interest, which also improves the MRI reconstruction in step 460.

Figure 5:
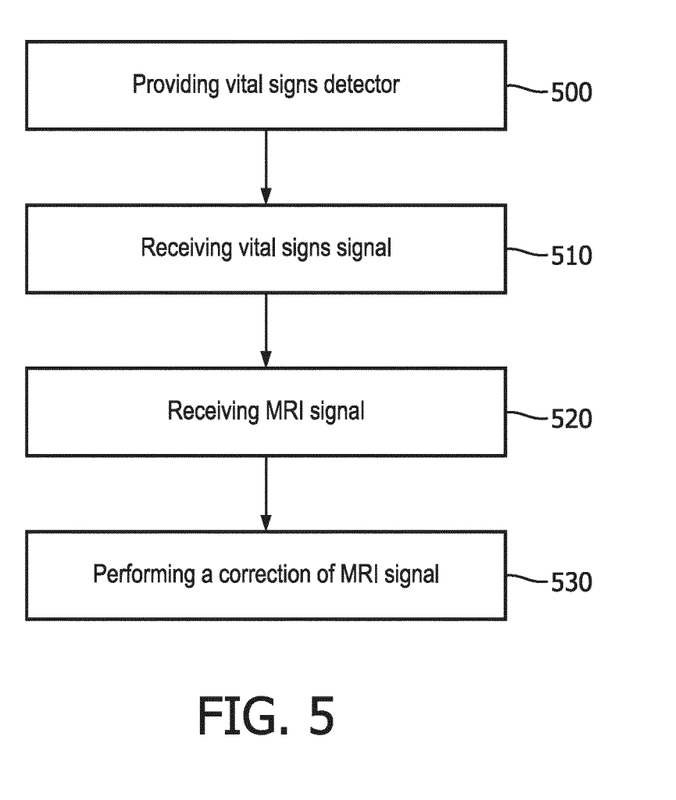
FIG. 5 shows a flowchart of a method for operating a system for the detection of vital signs in accordance with an embodiment of the invention.

FIG. 5 shows a flowchart of a method for operating a system for the detection of vital signs in accordance with an embodiment of the invention.

The method starts with step 500 in which a radio frequency (RF) transmit-receive coil 1 comprising a vital signs detector 3 is provided, wherein the radio frequency (RF) transmit-receive coil 1 and the vital signs detector 3 form a magnetic resonance (MR) imaging coil array.

In Step 510 at least one vital signs signal is received from the vital signs detector 3.

In step 520 at least one MRI signal is received from the radio frequency (RF) transmit-receive coil 1.

In step 530 a correction of the MM signal based on the vital signs signal is performed.

Figure 6:
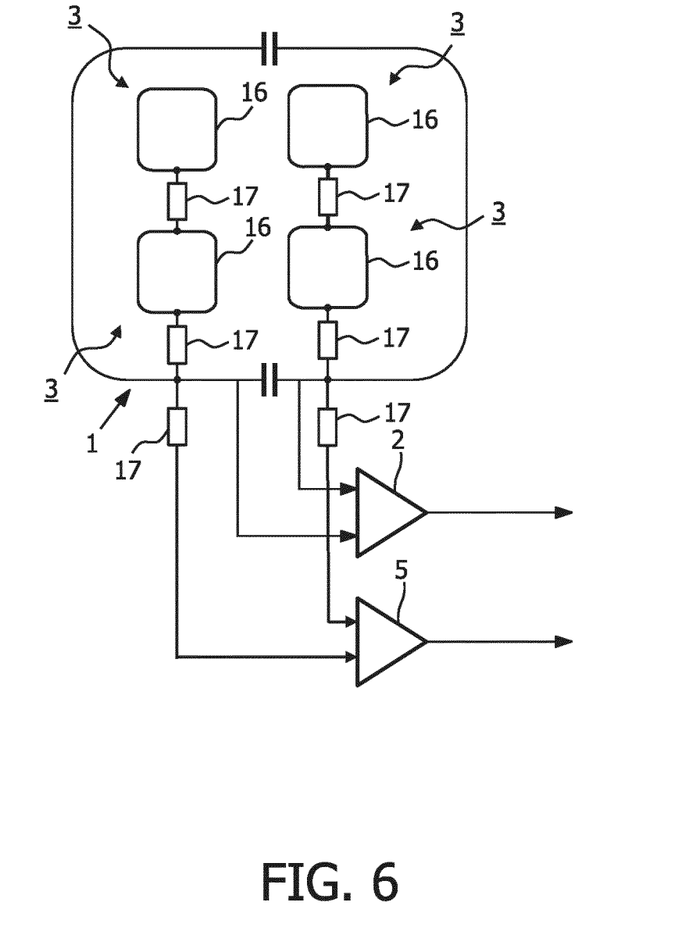
FIG. 6 shows vital signs detector patches with a RF transmit-receive coil and impedance circuits in accordance with an embodiment of the invention.

FIG. 6 shows vital signs detector patches 16 with a RF transmit-receive coil 1 and impedance circuits 17 in accordance with an embodiment of the invention. To increase the capacitance, the additional electrically conducting coil elements 4 forming the vital signs detectors 3 can be formed as patches 16 and combined with the RF transmit-receive coil 1. The patches can be e.g. ECG patches with electrocardiography (ECG) sensors the sensors being adapted for receiving ECG signals. Several patches 16 can be located inside the coil circumference or partly under the coil. The patches 16 are separated from each other in order to prevent B1 shielding effects from the excitation field of the MR body transmit coil. The individual patches 16 are connected via impedance circuits 17. The impedance circuits 17 can be RF chokes or parallel resonant circuits with a high impedance at the MRI frequency and a low impedance at frequencies for ECG and breathing. In FIG. 6 the signals are amplified and processed separately by different optimized amplifiers 2, 5 e.g. low noise amplifiers (LNA).

Figure 7:
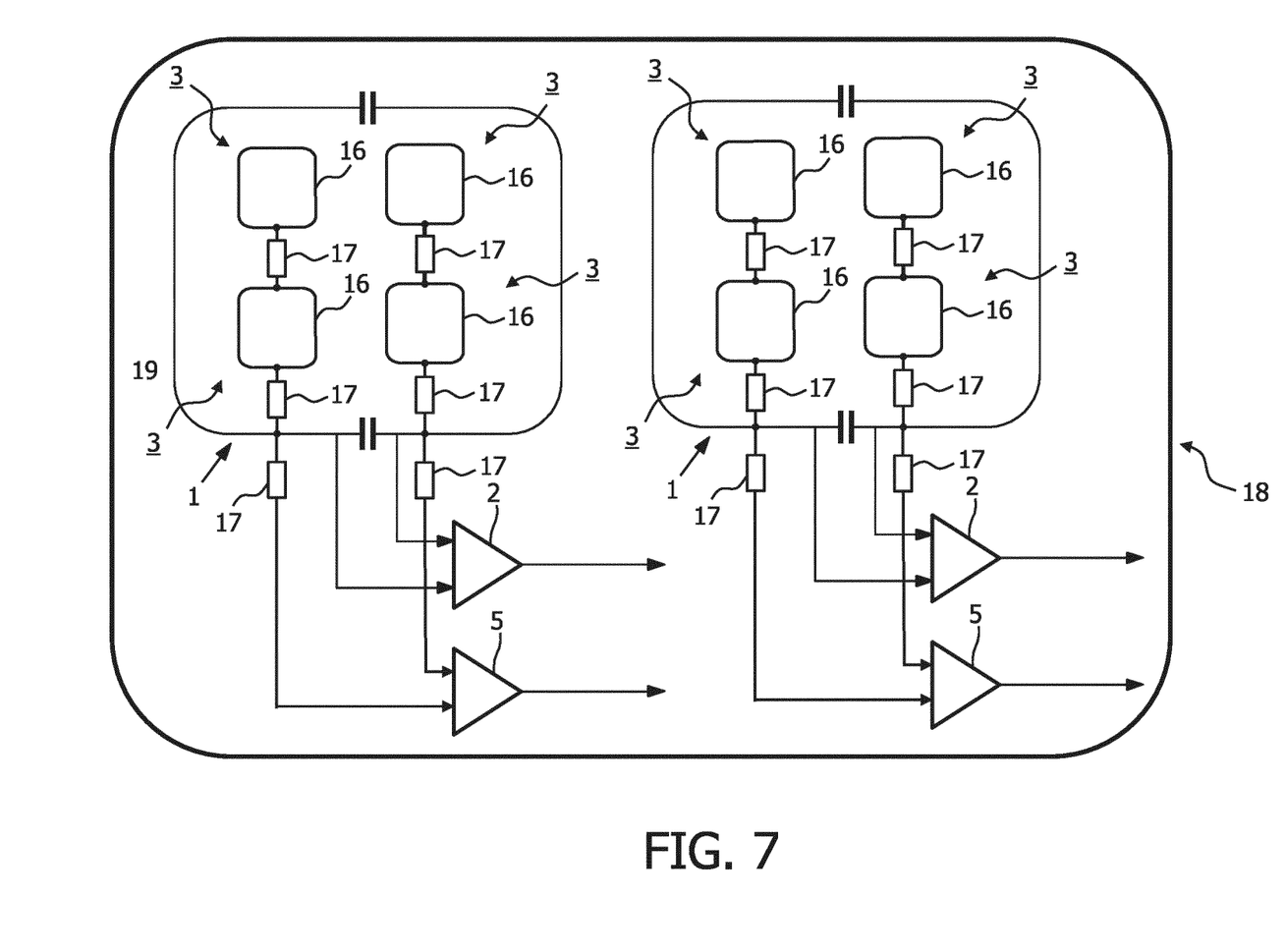
FIG. 7 shows a RF coil array with individual hybrid RF transmit-receive coils and vital signs detector patches in accordance with an embodiment of the invention.

FIG. 7 shows a RF coil array 18 with individual hybrid RF transmit-receive coils 1 and vital signs detector patches 16 in accordance with an embodiment of the invention. Each coil 1 does see an individual part of the human body. The individual signals of the vital signs detector patches 16 can be selected e.g. using a multiplexer.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Further, for the sake of clearness, not all elements in the drawings may have been supplied with reference signs.

REFERENCE SYMBOL LIST radio frequency (RF) transmit-receive coil 1
RF amplifier 2
capacitive vital signs detector 3
electrically conducting coil element 4
capacitive vital signs sensor amplifier 5
ADC for vital signs signal 6
ADC for MRI signal 7
signal processing unit 8
interface 9
match and detune circuit 10
diode 11
relaxation oscillator 12
microcontroller 13
multiplexer 14
control signal 15
vital signs detector patch 16
impedance circuit 17
RF coil array 18

The invention claimed is:

1. A radio frequency (RF) transmit-receive coil for a magnetic resonance (MR) imaging system, the RF transmit-receive coil comprising:
a vital signs detector for the detection of vital signs of a patient within the magnetic resonance (MR) imaging system, wherein the vital signs detector is integrated in the RF transmit-receive coil, wherein a pair of electrically conducting coil elements of the RF transmit-receive coil forms the vital signs detector, wherein the vital signs detector is a capacitive vital signs detector, the capacitive vital signs detector being adapted for receiving capacitive vital signs signals wherein the vital signs detector is configured to measure the respiration and/or cardiac activity and wherein the capacitive vital signs detector is an electrocardiography (ECG) sensor being adapted for receiving ECG signals.

2. The radio frequency (RF) transmit-receive coil of claim 1, wherein the pair of electrically conducting coil elements are covered with a material having a high permittivity.

3. The radio frequency (RF) transmit-receive coil of claim 1, wherein the capacitive vital signs detector and the RF transmit-receive coil are configured to process the capacitive vital signs signal and an MRI signal acquired by the RF transmit-receive coil in different frequency spaces.

4. The radio frequency (RF) transmit-receive coil of claim 1, wherein the vital signs detector is arranged beneath a patient support of a magnetic resonance (MR) imaging system.

5. A system for the detection of vital signs of a patient within a magnetic resonance (MR) imaging system, the system comprising:
a radio frequency (RF) transmit-receive coil with a vital signs detector according to claim 1, the system further comprising an output pre-amplifier for amplifying the capacitive vital signs signals, wherein the pair of electrically conducting coil elements is coupled to the output pre-amplifier, the system further comprising a digital signal processor, wherein the digital signal processor being adapted for further processing the amplified capacitive vital signs signals.

6. The system according of claim 5, wherein the digital signal processor is a software defined radio.

7. The system according to claim 5, comprising a relaxation oscillator and/or a microcontroller for the capacitive vital signs signals detection.

8. The system of claim 5, comprising a multiplexer for switching between different pairs of electrically conducting coil elements of the RF transmit-receive coil forming the vital signs detector.

9. A software package for upgrading a magnetic resonance imaging system, wherein the software package contains instructions stored on a non-transitory computer readable medium for controlling a radio frequency (RF) receiver system comprising a vital signs detector according to claim 8.

10. A magnetic resonance (MR) imaging system comprising a system for the detection of vital signs of a patient according to claim 1.

11. A method for operating the system for the detection of vital signs of a patient within a magnetic resonance imaging (MRI) system according to claim 4 comprising the following steps:
providing a radio frequency transmit-receive coil comprising a vital signs detector, wherein the radio frequency transmit-receive coil and the vital signs detector form a magnetic resonance imaging coil array,
receiving at least one vital signs signal from the vital signs detector,
receiving at least one MRI signal from the radio frequency (RF) transmit-receive coil,
performing a correction of the MRI signal based on the vital signs signal.

12. The method of claim 11, wherein, the performing a correction of the MRI signal based on the vital signs signal includes a correction based on a deep learning algorithm.

13. A software package for a magnetic resonance (MR) imaging system, wherein the software package includes instructions stored on a non-transitory computer readable medium for controlling a system for the detection of vital signs of a patient within a magnetic resonance (MR) imaging system according to claim 11.

* * * * *